(12) United States Patent
Margraf et al.

(10) Patent No.: US 10,180,352 B2
(45) Date of Patent: Jan. 15, 2019

(54) MEASURING LIGHT SOURCE, AND MEASURING SYSTEM FOR DETECTING A REFLECTION SPECTRUM

(71) Applicant: Carl Zeiss Spectroscopy GmbH, Jena (DE)

(72) Inventors: Joerg Margraf, Koenigsee-Rottenbach (DE); Thomas Keune, Jena (DE)

(73) Assignee: CARL ZEISS SPECTROSCOPY GMBH, Jena (DE)

( * ) Notice: Subject to any disclaimer, the term of this patent is extended or adjusted under 35 U.S.C. 154(b) by 0 days.

(21) Appl. No.: 15/694,318

(22) Filed: Sep. 1, 2017

(65) Prior Publication Data

US 2018/0066988 A1 Mar. 8, 2018

(30) Foreign Application Priority Data

Sep. 2, 2016 (DE) .................. 10 2016 116 405
Apr. 19, 2017 (DE) .................. 20 2017 102 313 U

(51) Int. Cl.
*G01J 3/10* (2006.01)
*G01J 3/42* (2006.01)
(Continued)

(52) U.S. Cl.
CPC .............. *G01J 3/10* (2013.01); *F21V 7/04* (2013.01); *F21V 7/043* (2013.01); *G01J 3/021* (2013.01);
(Continued)

(58) Field of Classification Search
CPC .......... G01J 3/10; G01J 3/42; G01J 2003/425; G01N 2201/061; G01N 21/4738
See application file for complete search history.

(56) References Cited

U.S. PATENT DOCUMENTS 3,874,799 A * 4/1975 Isaacs ................... G01J 3/0251
250/226
5,251,004 A * 10/1993 Doiron ...................... G01J 1/04
250/228
(Continued)

FOREIGN PATENT DOCUMENTS

DE 34 31 367 A1 2/1986
DE 202008012222 U1 1/2009
(Continued)

*Primary Examiner* — Sang H Nguyen
(74) *Attorney, Agent, or Firm* — Stuart H. Mayer; Mayer & Williams PC

(57) ABSTRACT

A measuring light source includes a hollow body having a diffusely reflective inner surface. Formed in the hollow body are a concave, concave mirror-shaped illumination space, a tubular light shaping space, and a concave, concave mirror-shaped light exit space, which have a shared axis. A light source for generating light is at least partially situated in the illumination space. The light exit space has a light exit. The illumination space and the light exit space with their concave mirror shapes are situated opposite one another and are connected by the tubular light shaping space. A diffusely reflecting reflective disk for reflecting the light, reflected from the inner surface of the hollow body situated in the light exit space, through the light exit to outside the hollow body is situated in the hollow body.

14 Claims, 5 Drawing Sheets

(51) Int. Cl.
*G01N 21/47* (2006.01)
*G01N 21/55* (2014.01)
*F21V 7/04* (2006.01)
*G01J 3/02* (2006.01)
*G01J 3/08* (2006.01)
*G01J 3/28* (2006.01)
*G01N 21/25* (2006.01)
*G01N 21/57* (2006.01)
*G01N 21/84* (2006.01)

(52) U.S. Cl.
CPC . G01J 3/08 (2013.01); G01J 3/28 (2013.01); G01J 3/42 (2013.01); G01N 21/255 (2013.01); G01N 21/474 (2013.01); G01N 21/4738 (2013.01); G01N 21/4785 (2013.01); G01N 21/55 (2013.01); *G01J 2003/102* (2013.01); *G01J 2003/425* (2013.01); *G01N 21/57* (2013.01); *G01N 2021/8411* (2013.01); *G01N 2201/061* (2013.01)

(56) References Cited

U.S. PATENT DOCUMENTS

| | | | | |
|---|---|---|---|---|
| 5,340,974 A | * | 8/1994 | Zalewski | G01J 1/08 250/205 |
| 5,359,406 A | * | 10/1994 | Suzuki | G01J 1/42 250/228 |
| 5,519,534 A | * | 5/1996 | Smith | A61N 5/062 250/228 |
| 5,745,234 A | * | 4/1998 | Snail | G01J 1/04 356/236 |
| 6,422,718 B1 | | 7/2002 | Anderson et al. | |
| 6,626,052 B1 | * | 9/2003 | Martin | G01N 17/004 250/228 |
| 7,329,028 B2 | * | 2/2008 | Wang | G01J 1/42 362/283 |
| 8,830,473 B2 | * | 9/2014 | Margraf | G01N 21/255 356/445 |
| 2010/0079747 A1 | * | 4/2010 | Park | G01J 1/02 356/236 |
| 2011/0098962 A1 | * | 4/2011 | Iguchi | G01N 21/31 702/104 |
| 2012/0229801 A1 | * | 9/2012 | Park | G01J 1/02 356/236 |
| 2013/0271764 A1 | | 10/2013 | Margraf et al. | |
| 2017/0211975 A1 | | 7/2017 | Margraf et al. | |

FOREIGN PATENT DOCUMENTS

| | | |
|---|---|---|
| DE | 10 2010 041 749 A1 | 4/2012 |
| DE | 10 2011 050 969 A1 | 5/2013 |
| DE | 10 2013 219 830 A1 | 4/2015 |
| DE | 10 2014 215 193 A1 | 2/2016 |

* cited by examiner

MEASURING LIGHT SOURCE, AND MEASURING SYSTEM FOR DETECTING A REFLECTION SPECTRUM

FIELD

The present invention relates to a measuring light source for generating measuring light having a uniform spatial illuminance distribution. The invention further relates to a measuring system for detecting an absolute reflection spectrum of a sample and for carrying out a reference measurement. The measuring system is used in particular for the spectroscopic analysis of surfaces in production processes in order to determine the color or luster of the surfaces, for example.

BACKGROUND

DE 10 2011 050 969 A1 discloses a device for the referenced measurement of reflected light, including a hollow body that has a diffusely scattering layer in its interior, and a light exit aperture. The device is switchable from a measurement position into a calibration position, as a result of which the light exit aperture is brought from a first detection axis into a second detection axis.

A measuring device is known from DE 10 2010 041 749 A1, having a cavity, extending in a longitudinal direction, with an opening that is to face toward a sample, and a plurality of openings situated in the longitudinal direction. A further opening is used for coupling in light.

U.S. Pat. No. 6,422,718 B1, DE 34 31 367 A1, and DE 20 2008 012 222 U1 disclose measuring light sources in various embodiments.

DE 10 2013 219 830 A1 teaches an optical device for reflection measurement under diffuse illumination, which includes a hollow body having a light-scattering surface in its interior, and a light exit aperture. The light exit aperture has a rotationally asymmetrical shape.

For detecting an absolute reflection spectrum, so-called VW systems and VN systems are known from the prior art which ensure that a reference measurement and a measurement of a sample differ only by the reflection on the sample.

DE 10 2014 215 193 A1 discloses a measuring system for detecting an absolute reflection spectrum of a sample. This measuring system includes a light source and a homogenizer for generating a uniform spatial illuminance distribution of the measuring light. The measuring system also includes a movable reflector and a receiver. The reflector is situated on the side of the sample as the light source. The homogenizer is preferably formed by an Ulbricht sphere or an Ulbricht tube, or by a sphere-cylinder design. In this measuring system, if the distance from the sample changes or the sample tilts, the Ulbricht sphere results in measuring errors of greater than 1% in the absolute measurement, which for many applications is too high. However, outside of laboratory conditions, in particular for inline measurements in production processes, changes in sample distance and sample tilting are unavoidable.

Proceeding from the prior art, the object of the present invention is to increase the uniformity of the spatial illuminance distribution of a measuring light in comparison to the measuring light that is generatable with an Ulbricht sphere, in order to able to carry out accurate measurements of an absolute reflection spectrum with less effort.

The stated object is achieved by a measuring light source according to appended Claim 1. The stated object is further achieved by a measuring systems according to the other appended independent Claims 6 and 11.

The measuring light source according to the invention is used for generating measuring light having a uniform spatial illuminance distribution. It is possible, for example, to conduct spectrometric analyses of surfaces by use of the measuring light source according to the invention. The measuring light source includes, first of all, a hollow body having a diffusely reflective inner surface. The interior is divided into a concave illumination space having the shape of a concave mirror, a tubular light shaping space, and a concave light exit space having the shape of a concave mirror, which have a shared axis. Thus, the concave mirror shape of the illumination space, the tubular shape of the light shaping space, and the concave mirror shape of the light exit space each have an axis, these axes coinciding and forming the axis of the hollow body and of the measuring light source. Although the illumination space and the light exit space each have a concave mirror shape, as mentioned they are diffusely reflective, and in this regard do not represent a concave mirror. The illumination space and the light exit space may also each be characterized as a concavely shaped reflector or as a concavely shaped Lambertian reflector.

A light source is at least partially situated in the illumination space. In any case, the light source is situated in such a way that it radiates light into the illumination space; the light source may be situated partially outside the illumination space. The light source is preferably situated on or in the axis. The light source is preferably situated in a focal point of the concave mirror shape of the illumination space.

The light exit space has a light exit through which light may pass from the light exit space to outside the hollow body. The light exit is preferably situated on or in the axis. The light passing from the light exit forms the measuring light that is generatable by the measuring light source.

The illumination space and the light exit space are situated with their concave mirror shapes, i.e., their concave reflector shapes, opposite one another. The inner sides of the concave mirror shapes or of the concave reflector shapes are oriented toward one another. The illumination space and the light exit space are preferably situated with their concave mirror shapes mirror-symmetrically opposite one another. However, the illumination space and the light exit space do not contact one another. The tubular light shaping space is situated between the illumination space and the light exit space, and connects the light shaping space and the illumination space. Light can thus pass into the light exit space via the light shaping space due to reflections on the inner surface of the hollow body from the illumination space. The concave mirror shape of the illumination space is preferably the same as the concave mirror shape of the light exit space. The concave mirror shape of the illumination space preferably merges continuously into the tubular shape of the light shaping space. The tubular shape of the light shaping space preferably merges continuously into the concave mirror shape of the light exit space. Thus, the extent of the concave mirror shape of the illumination space, the extent of the tubular shape of the light shaping space, and the extent of the concave mirror shape of the light exit space are preferably equal.

According to the invention, a diffusely reflecting reflective disk is situated in the hollow body. The reflective disk is used for reflecting the light that is reflected from the inner surface of the hollow body situated in the light exit space, so that the light is cast through the light exit to the outside of the hollow body. The reflective disk is preferably flat. The reflective disk is preferably nontransparent, i.e., opaque. The reflective disk shades the light exit from the light source, so that the light from the light source cannot directly pass through the light exit.

One particular advantage of the measuring light source according to the invention is that, due to the easily implemented modification of an Ulbricht sphere or an Ulbricht sphere-like sphere-cylinder arrangement, it allows generation of a measuring light having an extremely uniform spatial illuminance distribution.

The measuring light that is generatable with the measuring light source according to the invention has a deviation of its spatial illuminance distribution which preferably is no greater than 0.2%. This makes inline use of the measuring light source possible during a measurement of an absolute reflection spectrum, since the variance in the sample distance, the variation in the sample thickness, and tilting of the sample are tolerable.

The light that is generatable by the light source is preferably reflected in the hollow body three times before it exits the light exit. One of the at least three reflections takes place on the reflective disk. The light that is generatable by the light source is particularly preferably reflected in the hollow body at least four times before it exits the light exit. A majority of the light is reflected in the hollow body many times before it exits the light exit.

The diffusely reflective inner surface of the hollow body and the diffusely reflective surface of the reflective disk have a reflectance of preferably at least 96%, particularly preferably at least 98%, in the overall light spectrum. The diffusely reflective inner surface of the hollow body and the diffusely reflective surface of the reflective disk are preferably formed by a coating made of polytetrafluoroethylene (PTFE).

The light source preferably includes one or more light source elements, each of which is preferably formed by a halogen lamp, a flash lamp, a xenon flash lamp, a deuterium lamp, an IR emitter, an LED that emits in particular white light, a UV cathode, or a UV LED. The light source particularly preferably includes several of the light source elements, which preferably are formed by a halogen lamp, a white LED, and two UV LEDs. The individual light source elements preferably have the capability for independent switching and/or power modification.

The light source preferably includes one or more optical fibers via which the light source elements may radiate into the illumination space. The particular light source elements are not situated in the illumination space, but, rather, may be situated outside the illumination space. In any case, the optical fiber(s) of the light source open(s) into the illumination space, so that the light source is partially situated in the illumination space.

In preferred embodiments of the measuring light source according to the invention, the reflective disk is situated on the axis and perpendicular to the axis. The axis is preferably situated in the middle of the reflective disk. The reflective disk preferably has an oval, ellipsoidal, or circular shape.

The reflective disk is preferably designed to prevent the light source from directly illuminating the inner surface of the hollow body situated in the light exit space. The reflective disk is thus designed for shading the inner surface of the hollow body situated in the light exit space from the light source. This property of the opaque reflective disk is due essentially to the fact that it is designed for reflecting the light, which is reflected by the inner surface of the hollow body situated in the light exit space, through the light exit, for which purpose it is preferably situated on the axis and thus already shades the inner surface of the hollow body situated in the light exit space from the light source. In other respects, the position and the size of the reflective disk as well as the cross section and the length of the light shaping space must be coordinated with one another in such a way that the inner surface of the hollow body situated in the light exit space is shaded from the light source.

On its outer circumference the reflective disk preferably has a collar facing the light exit space. The collar shades the reflective disk from incident light striking laterally at a very small angle, and preferably has the same diffusely reflective surface as the overall cavity.

The reflective disk is preferably situated in the light exit space, in the light shaping space, or at a transition from the light exit space to the light shaping space. The latter-mentioned position is best suited for reflecting the light that is reflected from the inner surface of the hollow body situated in the light exit space and for guiding it through the light exit.

A light-shaping cylinder, on whose end facing the light exit space the reflective disk is situated, is preferably situated inside the light shaping space. The light-shaping cylinder preferably has the same diffusely reflective surface as the overall cavity. The light-shaping cylinder is preferably centrally situated in the tubular shape of the light shaping space. The light-shaping cylinder is preferably situated in the axis of the hollow body. The axis of the hollow body preferably also forms an axis of the light-shaping cylinder. The light-shaping cylinder preferably has the same axial length as the light shaping space. The light-shaping cylinder preferably has an oval, ellipsoidal, or circular cross section. The light-shaping cylinder is not irradiatable by the light source.

A hollow cylindrical reflection area that is designed for shaping and guiding the light exiting the illumination space toward the light exit space is provided between the lateral surface of the light-shaping cylinder and the inner lateral surface of the light shaping space. In addition, the light-shaping cylinder is designed to prevent the light source from directly illuminating the inner surface of the hollow body situated in the light exit space. As a result, the light-shaping cylinder is designed to shade the inner surface of the hollow body situated in the light exit space from the light source.

The light-shaping cylinder is preferably hollow at its axial end facing the illumination space, for example in order to provide further installation space for the light source.

The reflective disk and/or the light-shaping cylinder are/is preferably fastened via webs to the inner surface of the hollow body in the light shaping space. The webs preferably extend radially with respect to the axis. The webs preferably have the same diffusely reflective surface as the overall cavity.

The concave mirror shape of the illumination space is preferably formed by a hollow hemisphere. Alternatively, the concave mirror shape of the illumination space preferably has an ellipsoidal or oval cross section perpendicular to the axis.

The concave mirror shape of the light exit space is preferably formed by a hollow hemisphere. Alternatively, the concave mirror shape of the light exit space preferably has an ellipsoidal or oval cross section perpendicular to the axis.

The light exit is preferably closed by a protective glass, so that the cavity is closed by this protective glass.

The measuring system according to the invention is used for detecting an absolute reflection spectrum of a sample. The measuring system is used, for example, for an inline measurement in a production process for large coated surfaces, such as glass disks or films, in order to inspect the surface. A reference sample is not necessary for detecting the absolute reflection spectrum. The measuring system therefore also allows a reference measurement of a measuring light that is used.

A first embodiment of the measuring system includes, firstly, the measuring light source according to the invention for generating the measuring light having a uniform spatial illuminance distribution.

The first embodiment of the measuring system also includes an optical receiver, situated opposite from the measuring light source, for receiving light. The light to be received is the measuring light of the measuring light source after it has traveled a path over the sample, or a reference path. An entry opening of the receiver and an exit opening of the measuring light source are aligned with one another, except for an offset.

The first embodiment of the measuring system is designed to be situated parallel to a surface of the sample. In particular, the axis of the measuring light source is to be situated parallel to the surface of the sample, namely, with an offset with respect to the surface of the sample.

The first embodiment of the measuring system includes a first mirror that is situated on the axis of the measuring light source and aligned for reflecting the measuring light of the measuring light source, exiting the light exit, onto the sample. The first mirror is preferably rigidly mounted.

The first embodiment of the measuring system also includes a second mirror that is adjustable in at least two positions. In a first position, the second mirror is aligned for reflecting the measuring light, reflected from the first mirror, to the receiver. The first position is thus designed for a reference measurement, since on its path from the measuring light source to the receiver, the measuring light passes the components of the measuring system, in particular the first and second mirrors, but not the sample. In this regard, the first mirror is also aligned for reflecting the measuring light of the measuring light source, exiting the light exit, onto the second mirror. In a second position, the second mirror is aligned for reflecting the measuring light, reflected from the sample, to the receiver. The second position is thus designed for a reflection measurement, since on its path from the measuring light source to the receiver, the measuring light is reflected from the sample.

The measuring light source, the receiver, the first mirror, and the second mirror are preferably situated together on one side of the sample. Correspondingly, the measuring light source, the receiver, the first mirror, and the second mirror are designed so that they are situated together on one side of the sample.

One particular advantage of the first embodiment of the measuring system according to the invention is that it may have a very compact design. The measuring light source and the receiver may be situated in one plane with only a slight offset, while the first mirror and the second mirror may be positioned in a space-saving manner between the measuring light source and the receiver.

The optical receiver is preferably formed by an optical sensor, such as a spectrometer in particular, or is formed at least by an optical input of the optical sensor. For example, the optical receiver may be formed by an input optical system to which an optical fiber that leads to a spectrometer is connected.

The receiver has an axis in which it receives incident light. In the first embodiment of the measuring system according to the invention, the axis of the receiver and the axis of the measuring light source are particularly preferably situated in parallel, and have an offset, i.e., are spaced apart from one another. However, this offset may be small. The offset is preferably smaller than a maximum extension of the hollow body in a direction perpendicular to the axis of the measuring light source. The second mirror is preferably situated on the axis of the receiver.

In the first embodiment of the measuring system according to the invention, the first mirror is preferably inclined toward the sample at an angle of 45° with respect to the axis of the measuring light source. The measuring light from the measuring light source is thus deflected by 90° with respect to the axis of the measuring light source, and when the second mirror is in the second position, may strike the surface of the sample perpendicularly.

In the first embodiment of the measuring system according to the invention, the second mirror is preferably to be adjusted by pivoting the second mirror from its first position into its second position, and vice versa. The second mirror is thus preferably stationary but rotatable. The axis of this pivoting movement is preferably formed by one of the four sides of the preferably rectangular second mirror. The axis of this pivoting movement is preferably perpendicular to the axis of the receiver and parallel to the surface of the sample.

In the first embodiment of the measuring system according to the invention, the second mirror in its first position is preferably inclined toward the first mirror at an angle of 45°±5° with respect to the axis of the receiver. The measuring light reflected from the first mirror, which is preferably oriented at an angle of 90° with respect to the axis of the measuring light source or of the receiver, is thus deflected again by 90°, so that it may pass to the receiver in the axis of the optical receiver.

In the first embodiment of the measuring system according to the invention, the second mirror in its second position is preferably inclined toward the sample at an angle of 45°±5° with respect to the axis of the receiver. The measuring light reflected from the sample is thus deflected, so that it may pass to the receiver in the axis of the receiver.

In the first embodiment of the measuring system according to the invention, the second mirror is preferably pivotable between its first position, its second position, and a third position. The third position is designed for a transmission measurement of the sample. For this purpose, the measuring system also includes a fourth mirror that is situated on the side of the sample opposite from the first mirror. The fourth mirror is designed for reflecting the measuring light, reflected from the first mirror and transmitted by the sample, back to the sample and to the second mirror. The sample thus transmits the measuring light exactly twice, namely, a first time, before it strikes the fourth mirror, and a second time, after it has been reflected from the fourth mirror. The twice-transmitted measuring light is then reflected from the second mirror to the receiver. The fourth mirror is preferably rigidly mounted. The fourth mirror is preferably situated parallel to the axis of the measuring light source and preferably parallel to the flat sample.

In the first embodiment of the measuring system according to the invention, the second mirror in its third position is further inclined with respect to the sample than in its second position. The second mirror in its third position is preferably inclined toward the sample at an angle between 40° and 70°, in particular between 47° and 60°, with respect to the axis of the receiver.

The second mirror is preferably pivotable between its first position, its second position, and a fourth position, the fourth position being designed for a dark measurement. The second mirror does not cast measuring light onto the receiver in this fourth position. For this purpose, the second mirror in its fourth position is preferably oriented toward the receiver perpendicularly with respect to the axis of the receiver. The dark measurement together with the reference measurement is used for balancing the measuring system in order to be able to make an accurate measurement of the absolute reflection spectrum, using the measuring system.

In the first embodiment of the measuring system according to the invention, the second mirror is preferably pivotable between its first position, its second position, its third position, and its fourth position.

The measuring light source, the receiver, the first mirror, and the second mirror preferably form a measuring head. The measuring head includes a housing in which the measuring light source, the receiver, the first mirror, and the second mirror are situated. The housing has a measuring opening through which the measuring light reflected from the first mirror may pass outwardly, and through which the measuring light reflected from the sample may pass inwardly to the second mirror.

A second embodiment of the measuring system includes, firstly, a measuring light source for generating the measuring light having a uniform spatial illuminance distribution. The measuring light source has a light exit that is situated on or in an axis of the measuring light source. The light exiting the light exit forms the measuring light that is generatable by the measuring light source. This measuring light source is preferably formed by the above-described measuring light source according to the invention.

The second embodiment of the measuring system also includes an optical receiver, situated opposite from the measuring light source, for receiving light. The light to be received is the measuring light of the measuring light source after it has traveled a path over the sample, or a reference path. An entry opening of the receiver and an exit opening of the measuring light source are aligned with one another, except for a possible offset. The receiver has an axis in which it receives incident light.

The second embodiment of the measuring system is designed to be situated parallel to a surface of the sample. In particular, the axis of the measuring light source is to be situated parallel to the surface of the sample, namely, with an offset with respect to the surface of the sample.

The second embodiment of the measuring system includes a first mirror that is situated on or in the axis of the optical receiver and aligned for reflecting the light reflected from the sample to the optical receiver. The first mirror is preferably rigidly mounted.

The second embodiment of the measuring system also includes a second mirror that is adjustable in at least two positions. In a first position, the second mirror is aligned for reflecting the measuring light, exiting the light exit, onto the first mirror. The first position is thus designed for a reference measurement, since on its path from the measuring light source to the receiver, the measuring light passes the components of the measuring system, in particular the first and second mirrors, but not the sample. In this regard, the first mirror is also aligned for reflecting the light reflected from the second mirror to the optical receiver. In a second position, the second mirror is aligned for reflecting the measuring light, exiting the light exit, onto the sample. The second position is thus designed for a reflection measurement, since on its path from the measuring light source to the receiver, the measuring light is reflected from the sample.

The measuring light source, the receiver, the first mirror, and the second mirror are preferably situated together on one side of the sample. Correspondingly, the measuring light source, the receiver, the first mirror, and the second mirror are designed to be situated together on one side of the sample.

One particular advantage of the second embodiment of the measuring system according to the invention is that it may have a very compact design. The measuring light source and the receiver may be situated in one plane with only a slight offset, while the first mirror and the second mirror may be positioned in a space-saving manner between the measuring light source and the receiver.

The second embodiment of the measuring system is suitable for measuring samples having greatly different thicknesses. The measuring system according to the invention is preferably designed for measuring a sample having a thickness of up to 20 mm. The measuring system according to the invention is preferably designed for measuring glass disks. Of course, samples having a negligibly small thickness in the nm or μm range may also be measured using the measuring system according to the invention.

The optical receiver is preferably formed by an optical sensor, such as a spectrometer in particular, or is formed at least by an optical input of the optical sensor. For example, the optical receiver may be formed by an input optical system to which an optical fiber that leads to a spectrometer is connected.

In the second embodiment of the measuring system according to the invention, the axis of the receiver and the axis of the measuring light source are particularly preferably situated in parallel, and have an offset, i.e., are spaced apart from one another. However, this offset may be small. The offset is preferably smaller than one-half the maximum extension of the measuring light source in a direction perpendicular to the axis of the measuring light source.

The second mirror in its first position and in its second position is situated in each case on or in the axis of the measuring light source, so that the measuring light exiting the light exit strikes the second mirror.

In the second embodiment of the measuring system according to the invention, the first mirror is preferably inclined toward the sample at an angle of 45°±5° with respect to the axis of the optical receiver. When the second mirror is not in its first position, the measuring light that is reflected from the sample and that strikes the first mirror is thus deflected by approximately 90° and strikes the optical receiver.

In the second embodiment of the measuring system according to the invention, the second mirror is preferably to be adjusted by pivoting the second mirror from its first position into its second position, and vice versa. The second mirror is thus preferably stationary but rotatable or pivotable. The axis of this pivoting movement is preferably formed by one of the four sides of the preferably rectangular second mirror. The axis of this pivoting movement is preferably perpendicular to the axis of the measuring light source and parallel to the surface of the sample. The axis of this pivoting movement is preferably situated between the axis of the measuring light source and the axis of the optical receiver.

In the second embodiment of the measuring system according to the invention, the second mirror in its first position is preferably inclined and oriented toward the first mirror at an angle of 50°±5° with respect to the axis of the measuring light source. The measuring light exiting the light exit, which is preferably situated in the axis of the measuring light source, is thus deflected by approximately 90° by the second mirror, so that it strikes the first mirror approximately perpendicularly with respect to the axis of the optical receiver, from which it is once again deflected by 90°, so that it strikes the optical receiver.

The second mirror in its second position is preferably inclined and oriented toward the sample at an angle of 50°±5° with respect to the axis of the measuring light source. The measuring light exiting the light exit is thus deflected so that it strikes the sample.

In the second embodiment of the measuring system according to the invention, the second mirror is preferably adjustable between its first position, its second position, and a third position. The third position is designed for a transmission measurement of the sample. For this purpose, the measuring system also includes a third mirror that is situated on the axis of the measuring light source and oriented toward the sample for reflecting the measuring light exiting the light exit. The third mirror is preferably rigidly mounted. The third mirror is preferably inclined toward the sample at an angle of 45°±5° with respect to the axis of the measuring light source. The second embodiment of the measuring system also includes a fourth mirror that is situated on the side of the sample opposite from the third mirror. The fourth mirror is aligned for reflecting the measuring light, reflected from the third mirror and transmitted by the sample, back to the sample and to the first mirror. The sample thus transmits the measuring light exactly twice, namely, a first time, before it strikes the fourth mirror, and a second time, after it has been reflected from the fourth mirror. The twice-transmitted measuring light is then reflected from the first mirror to the optical receiver. The fourth mirror is preferably rigidly mounted. The fourth mirror is preferably situated parallel to the axis of the measuring light source and preferably parallel to the flat sample.

In the second embodiment of the measuring system according to the invention, the second mirror is preferably adjustable by pivoting between its first position, its second position, and its third position.

In the second embodiment of the measuring system according to the invention, the second mirror in its third position is aligned in such a way that it enables a beam path from the light exit to the third mirror. Thus, the second mirror in its third position is preferably not situated in the beam path. The second mirror in its third position is preferably inclined at an angle between −20° and 20° with respect to the axis of the measuring light source, and is spaced apart from this axis.

In the described preferred embodiments, the second mirror must be pivoted by an angle of preferably 60°±20°, more preferably 60°±5°, for changing from its second position, which is suitable for a reflection measurement, to its third position, which is suitable for a transmission measurement, and vice versa. This comparatively large pivot angle results in a high photometric accuracy in particular for the transmission measurement, since skewing of the measurement by reflection signals is largely avoided in the transmission measurement.

In the second embodiment of the measuring system according to the invention, the second mirror is preferably adjustable between its first position, its second position, and a fourth position, the fourth position being designed for a dark measurement. The second mirror does not cast measuring light onto the sample in this fourth position. The second mirror in its fourth position is aligned in such a way that it enables a beam path from the sample to the first mirror. Thus, the second mirror in its fourth position is preferably not situated in the beam path from the sample to the first mirror. In the fourth position, the second mirror is preferably aligned in such a way that it reflects the measuring light, exiting the light exit, back to the light exit. For this purpose, the second mirror in its fourth position is preferably aligned perpendicularly with respect to the axis of the measuring light source. Measuring light is not directed onto the sample from any of the mirrors. The dark measurement together with the reference measurement is used for balancing the measuring system in order to be able to make an accurate measurement of the absolute reflection spectrum, using the measuring system.

In the second embodiment of the measuring system according to the invention, the second mirror is preferably adjustable by pivoting between its first position, its second position, and its fourth position.

The second mirror is preferably adjustable between its first position, its second position, its third position, and its fourth position. The second mirror is preferably pivotable between its first position, its second position, its third position, and its fourth position.

The measuring light source, the receiver, the first mirror, the second mirror, and optionally the third mirror preferably form a measuring head. The measuring head includes a housing in which the measuring light source, the receiver, the first mirror, the second mirror, and optionally the third mirror are situated. The housing has a measuring opening through which the measuring light reflected from the second mirror and optionally the measuring light reflected from the third mirror second may pass outwardly, and through which the measuring light reflected from the sample and optionally the measuring light reflected from the fourth mirror may pass inwardly to the first mirror.

The measuring light source in the described embodiments of the measuring system according to the invention is preferably formed by one of the described preferred embodiments of the measuring light source according to the invention. In other respects, the described embodiments of the measuring system according to the invention preferably also have other features, which are stated in conjunction with the measuring light source according to the invention and its preferred embodiments.

BRIEF DESCRIPTION OF THE DRAWINGS

Further particulars and refinements of the invention result from the following description of preferred embodiments of the invention, with reference to the drawings, which show the following.

DETAILED DESCRIPTION

Figure 1:
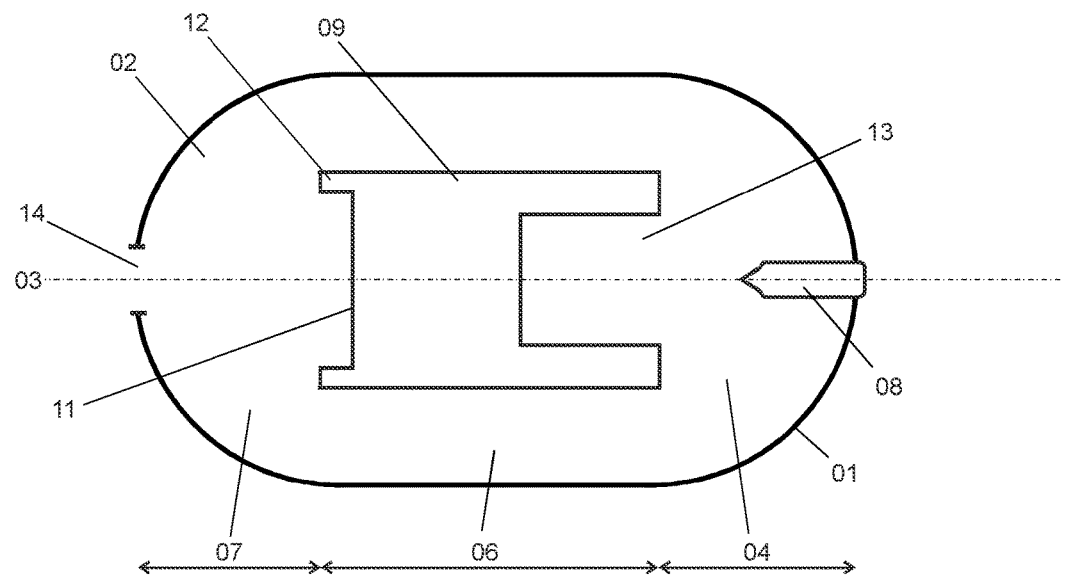
FIG. 1 shows a cross section of one preferred embodiment of a measuring light source according to the invention.

FIG. 1 shows a cross section of one preferred embodiment of a measuring light source according to the invention. The measuring light source, similarly to an Ulbricht sphere, has a hollow body 01 in which a cavity 02 is formed that has a diffusely reflective surface with a reflectance of at least 98% in the overall light spectrum. For this purpose, the inner surface of the hollow body 01 in the cavity 02 is coated with PTFE. The cavity 02 extends along an axis 03.

The cavity 02 in the hollow body 01 is divided into three axial sections, namely, a concave mirror-shaped illumination space 04, a tubular light shaping space 06, and a concave mirror-shaped light exit space 07.

Situated in the concave mirror-shaped illumination space 04 in the axis 03 is a light source 08 that includes a halogen lamp, a white LED, and two UV LEDs, not illustrated in detail. A light-shaping cylinder 09, which has the same axial length as the tubular light shaping space 06 and which has the diffusely reflective surface, is situated in the tubular light shaping space 06. The light-shaping cylinder 09 is fastened to the hollow body 01 via retaining webs 10 (for better clarity, shown only in FIG. 2). The light-shaping cylinder 09 has a diffusely reflecting, flat reflective disk 11 on its cover surface facing the light exit space 07. The reflective disk 11 is situated perpendicularly with respect to the axis 03, and centrally in the axis 03. The diffusely reflective surface of the reflective disk 11 is bordered by a collar 12. On its cover surface facing the illumination space 04, the light-shaping cylinder 09 has a hollow opening 13 which, for example, provides an installation space for longer embodiments of the light source 08. The light exit space 07 has a light exit 14 which likewise is situated in the axis 03.

Figure 2:
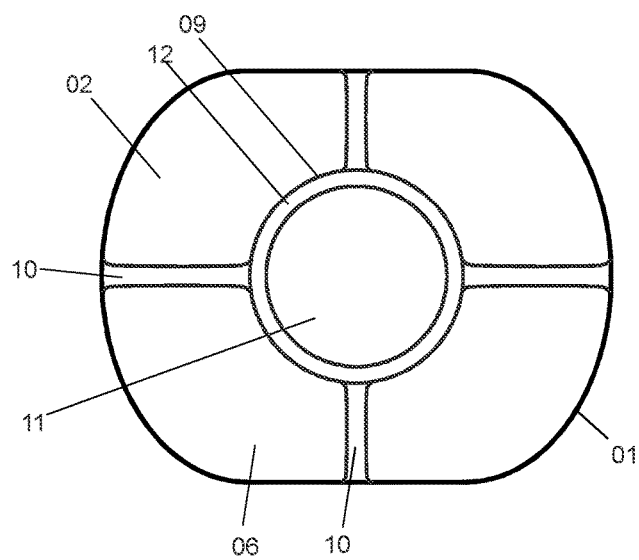
FIG. 2 shows another cross section of the measuring light source shown in FIG. 1.

FIG. 2 shows another cross section of the measuring light source shown in FIG. 1. This cross section is situated perpendicularly with respect to the axis 03 (shown in FIG. 1) and in the plane of the reflective disk 11. The retaining webs 10 are also shown in this cross-sectional illustration. In addition, it is apparent in this cross-sectional illustration that the hollow body 01 has an oval cross section, as the result of which it is possible to save some installation space in comparison to a circular cross section.

Figure 3:
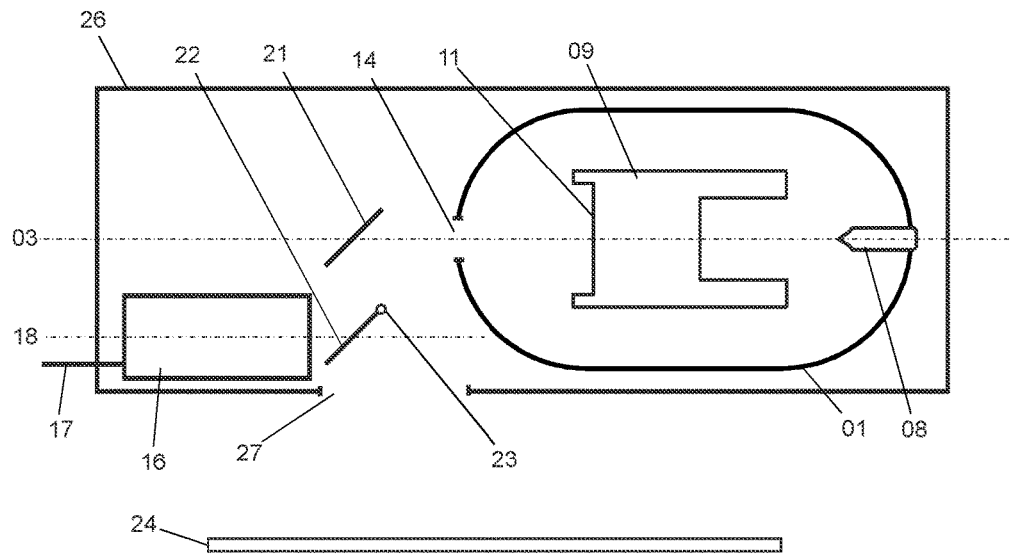
FIG. 3 shows a cross section of a first preferred embodiment of a measuring system according to the invention, in a position for a reference measurement.

FIG. 3 shows a cross section of a first preferred embodiment of a measuring system according to the invention. This first embodiment has the measuring light source shown in FIG. 1, including, among other things, the hollow body 01, the light source 08, and the reflective disk 11. The first preferred embodiment of the measuring system also includes an optical receiver 16, to which an optical fiber 17 that leads to a spectrometer (not shown) is connected. The optical receiver 16 has an axis 18 in which it may receive measuring light. The axis 18 of the optical receiver 16 is situated parallel to the axis 03 of the measuring light source.

The first preferred embodiment of the measuring system also includes a rigidly mounted first mirror 21 that is situated in the axis 03 of the measuring light source, so that the first mirror receives the measuring light that exits the light exit 14. The first mirror 21 is inclined at an angle of 45° with respect to the axis 03. The first mirror 21 is thus oriented toward a second mirror 22 that is pivotable about a pivot axis 23.

The second mirror 22 is shown in a first pivot position in which it is inclined at an angle of 45° with respect to the axis 18 of the optical receiver 16 and is oriented toward the optical receiver 16. The second mirror 22 thus reflects the measuring light, directed from the first mirror 21 onto the second mirror 22, directly to the receiver 16, so that the measuring light does not strike a sample 24 to be measured. The first position of the second mirror 22 is thus used for a reference measurement, since the measuring light that exits the measuring light source and is reflected from the two mirrors 21, 22 is measured by means of the receiver 16.

The first preferred embodiment of the measuring system includes a housing 26 in which the measuring light source, the receiver 16, and the two mirrors 21, 22 are situated, thus forming a measuring head. The housing 26 has a measuring opening 27 that is to be placed above the sample 24 to be measured. The sample 24 is to be situated parallel to the axis 18 of the optical receiver 16, and thus also parallel to the axis 03 of the measuring light source.

Figure 4:
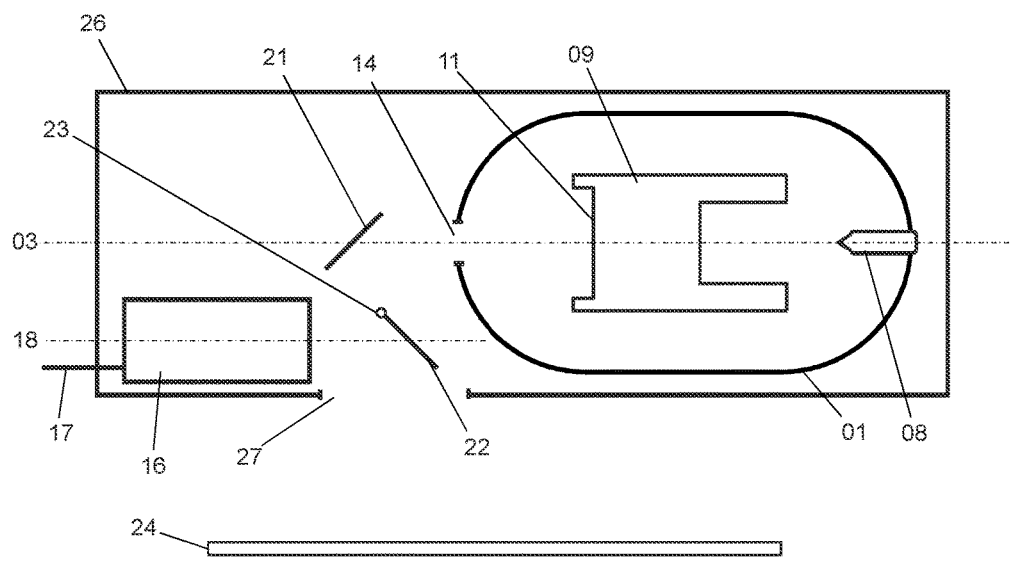
FIG. 4 shows the measuring system shown in FIG. 3 in a position for a reflection measurement.

FIG. 4 shows the first preferred embodiment of the measuring system shown in FIG. 3 in a position for a reflection measurement. For this purpose, the second mirror 22 is in a second pivot position in which it is inclined at an angle of 45° with respect to the axis 18 of the optical receiver 16 and is oriented toward the sample 24.

Figure 5:
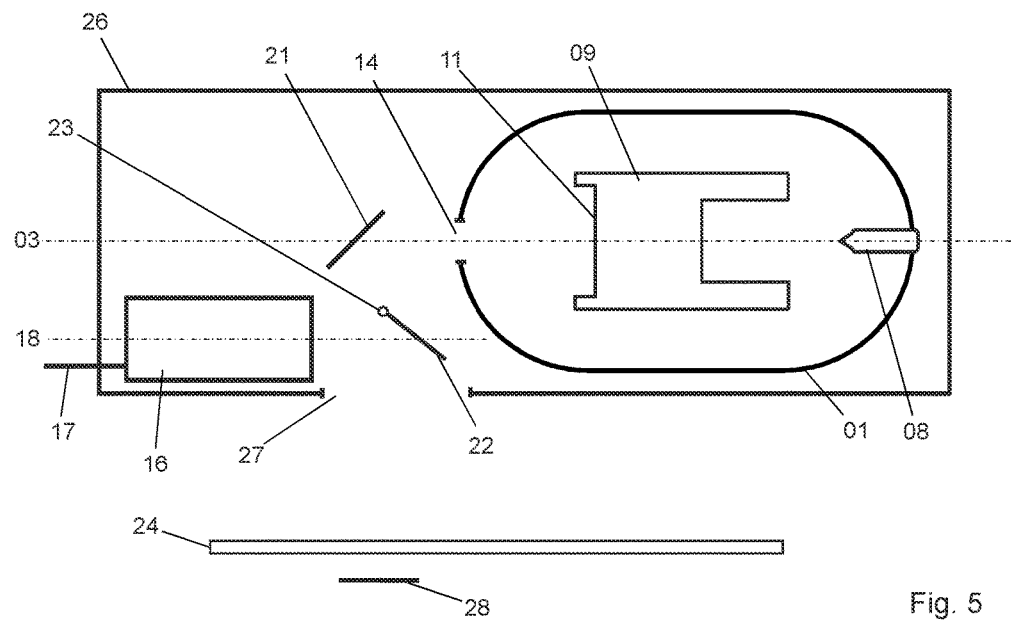
FIG. 5 shows the measuring system shown in FIG. 3 in a position for a transmission measurement.

FIG. 5 shows the first preferred embodiment of the measuring system shown in FIG. 3 in a position for a transmission measurement. For this purpose, the second mirror 22 is in a third pivot position in which it is inclined at an angle of approximately 50° with respect to the axis 18 of the optical receiver 16 and is oriented toward the sample 24. In this embodiment, the measuring system includes a fourth mirror 28 that is situated beneath the sample 24, i.e., on the side of the sample 24 opposite from the second mirror 22.

Figure 6:
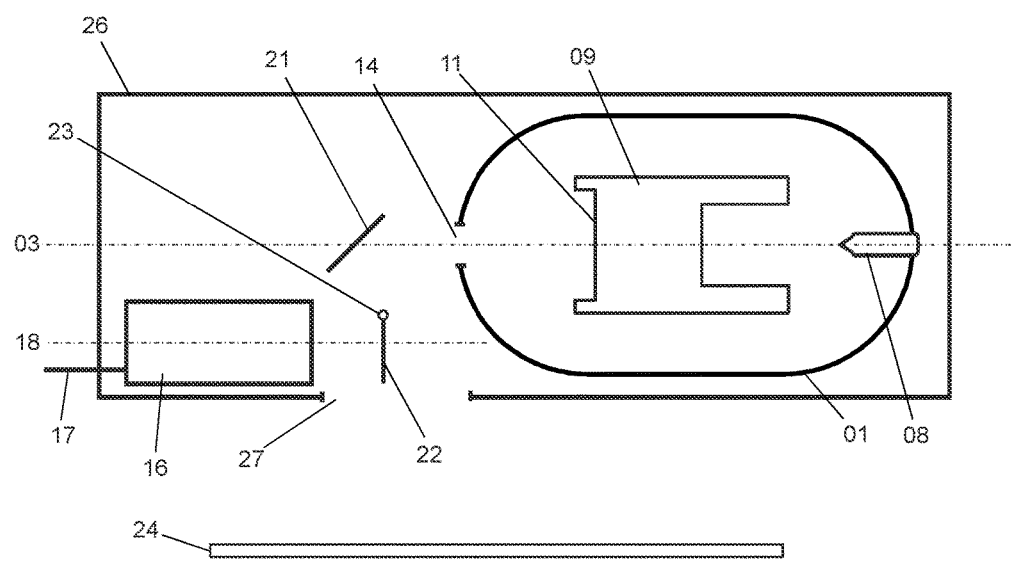
FIG. 6 shows the measuring system shown in FIG. 3 in a position for a dark measurement.

FIG. 6 shows the first preferred embodiment of the measuring system shown in FIG. 3 in a position for a dark measurement. For this purpose, the second mirror 22 is in a fourth pivot position in which it is situated perpendicularly with respect to the axis 18 of the optical receiver 16 and is oriented toward the optical receiver 16. In this position the optical receiver 16 receives no measuring light from the measuring light source.

Figure 7:
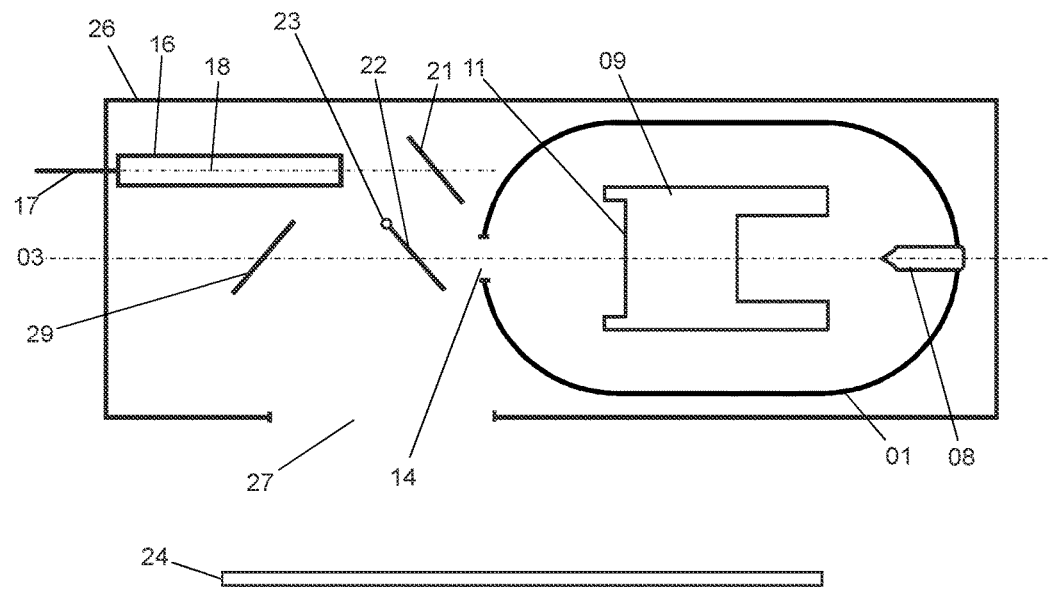
FIG. 7 shows a cross section of a second preferred embodiment of the measuring system according to the invention, in a position for a reference measurement.

FIG. 7 shows a cross section of a second preferred embodiment of the measuring system according to the invention. This embodiment has the measuring light source shown in FIG. 1, including, among other things, the hollow body 01, the light source 08, the reflective disk 11, and the light exit 14. This second embodiment once again includes the optical receiver 16 to which the optical fiber 17 that leads to the spectrometer (not shown) is connected. The optical receiver 16 is situated in the axis 18, in which it is able to receive measuring light. The axis 18 of the optical receiver 16 is situated parallel to the axis 03 of the measuring light source.

The second preferred embodiment of the measuring system also includes the rigidly mounted first mirror 21, which in this second embodiment is situated in the axis 18 of the optical receiver 16, so that it reflects measuring light striking it to the optical receiver 16. The first mirror 21 is inclined at an angle of approximately 45° with respect to the axis 18 of the optical receiver 16. The first mirror 21 is thus oriented toward the second mirror 22, which is pivotable about the pivot axis 23.

The second mirror 22 is shown in a first pivot position in which, in this second embodiment, it is inclined at an angle of 49° with respect to the axis 03 of the measuring light source and is oriented toward the first mirror 21. Since the second mirror 22 in its first pivot position is situated in the axis 03 of the measuring light source, the measuring light exiting the light exit 14 strikes the second mirror 22, from which it is reflected to the first mirror 21, from which it is further reflected to the optical receiver 16. Thus, the measuring light does not strike the sample 24 to be measured. In this second embodiment, the first position of the second mirror 22 is thus used for a reference measurement, since the measuring light that exits the measuring light source and is reflected from the two mirrors 21, 22 is measured by means of the optical receiver 16.

The second embodiment of the measuring system once again includes the housing 26 in which the measuring light source, the optical receiver 16, and the two mirrors 21, 22 are situated, thus forming a measuring head. The housing 26 has the measuring opening 27 that is to be placed above the sample 24 to be measured. The sample 24 is to be situated parallel to the axis 18 of the optical receiver 16, and thus also parallel to the axis 03 of the measuring light source.

Figure 8:
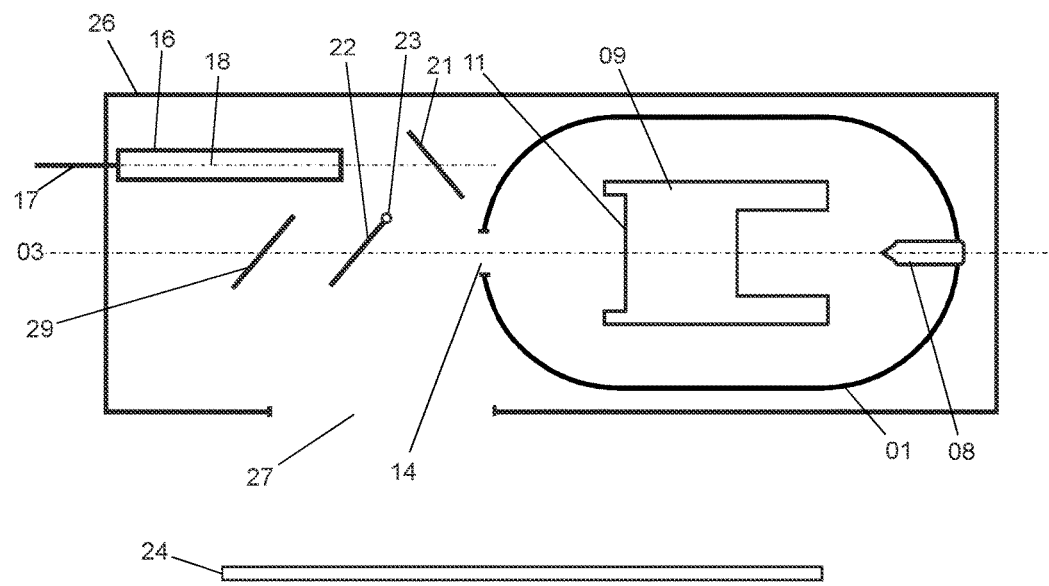
FIG. 8 shows the measuring system shown in FIG. 7 in a position for a reflection measurement.

FIG. 8 shows the second embodiment of the measuring system shown in FIG. 7 in a position for a reflection measurement. For this purpose, the second mirror 22 is in a second pivot position in which it is inclined at an angle of 50° with respect to the axis 03 of the measuring light source and is oriented toward the sample 24.

Figure 9:
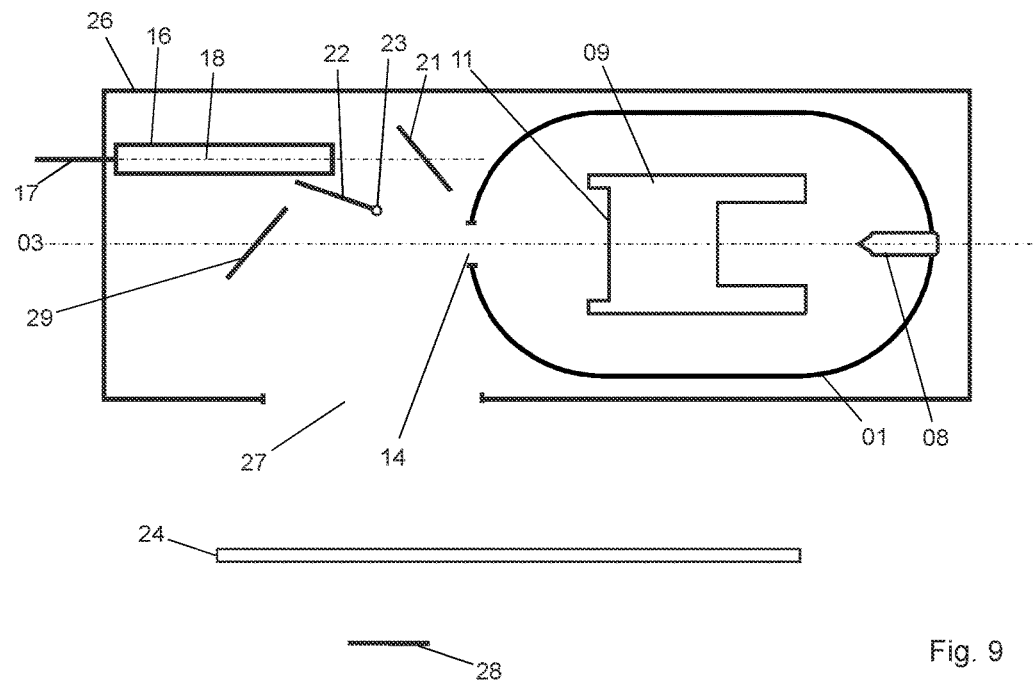
FIG. 9 shows the measuring system shown in FIG. 7 in a position for a transmission measurement.

FIG. 9 shows the second embodiment of the measuring system shown in FIG. 7 in a position for a transmission measurement. For this purpose, the second mirror 22 is in a third pivot position in which it is inclined at an angle of approximately 20° with respect to the axis 03 of the measuring light source and is spaced apart from this axis 03. In this second embodiment, the measuring system includes a third mirror 29, which is situated on the axis 03 of the measuring light source and is aligned for reflecting the measuring light, exiting the light exit 14, to the sample 24. The third mirror 29 is inclined toward the sample 24 at an angle of approximately 50° with respect to the axis 18 of the optical receiver 16. In this second embodiment, the measuring system also includes the fourth mirror 28, which is situated beneath the sample 24, i.e., on the side of the sample 24 opposite from the third mirror 29.

Figure 10:
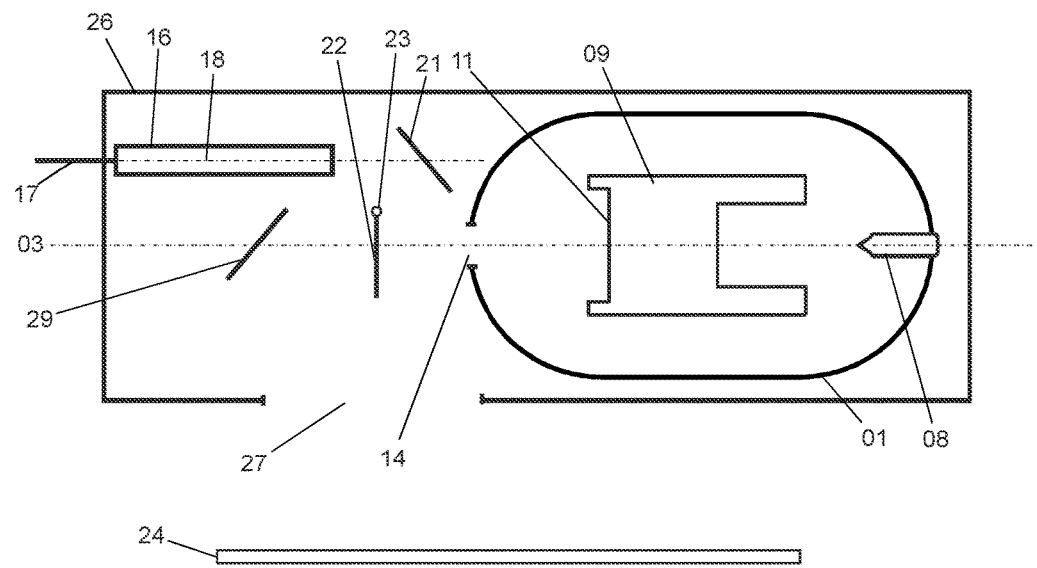
FIG. 10 shows the measuring system shown in FIG. 7 in a position for a dark measurement.

FIG. 10 shows the second embodiment of the measuring system shown in FIG. 7 in a position for a dark measurement. For this purpose, the second mirror 22 is in a fourth pivot position in which it is situated perpendicularly with respect to the axis 03 of the measuring light source and is situated in this axis 03. In this position the optical receiver 16 receives no measuring light from the measuring light source.

LIST OF REFERENCE NUMERALS 01 hollow body
02 cavity
03 axis of the measuring light source
04 illumination space
05 -
06 light shaping space
07 light exit space
08 light source
09 light-shaping cylinder
10 retaining webs
11 reflective disk
12 collar
13 opening
14 light exit
15 -
16 optical receiver
17 optical fiber
18 axis of the optical receiver
19 -
20 -
21 first mirror
22 second mirror
23 pivot axis
24 sample
25 -
26 housing
27 measuring opening
28 fourth mirror
29 third mirror

What is claimed is:

1. A measuring light source, comprising:
   a hollow body having a diffusely reflective inner surface in which a concave, concave mirror-shaped illumination space, a tubular light shaping space, and a concave, concave mirror-shaped light exit space are formed, which have a shared axis;
   a light source for generating light at least partially situated in the illumination space, wherein the light exit space has a light exit, and the illumination space and the light exit space have concave mirror shaped surfaces facing one another, the illumination space and the light exit space being connected by the tubular light shaping space, wherein a diffusely reflecting reflective disk for reflecting the light, reflected from the inner surface of the hollow body situated in the light exit space, through the light exit to outside the hollow body is situated in the hollow body; and
   wherein a diffusely reflective light-shaping cylinder is situated inside the light shaping space, the reflective disk being situated on the axial end of the light-shaping cylinder facing the light exit space.

2. The measuring light source according to claim 1, wherein the light that is generatable by the light source is reflected in the hollow body at least three times before it passes from the light exit, one of the at least three reflections taking place on the reflective disk.

3. The measuring light source according to claim 1, wherein the light source includes multiple light source elements, each of which is formed by a halogen lamp, a flash lamp, a xenon flash lamp, a deuterium lamp, an IR emitter, a white LED, a UV cathode, or a UV LED.

4. The measuring light source according to claim 1, wherein the light-shaping cylinder and/or the reflective disk are/is designed to shade the inner surface of the hollow body situated in the light exit space from the light source.

5. A measuring system for detecting an absolute reflection spectrum of a sample and for carrying out a reference measurement, comprising:
   a measuring light source according to claim 1;
   an optical receiver situated opposite from the measuring light source, for receiving measuring light;
   a first mirror that is situated on the axis of the measuring light source and aligned for reflecting the measuring light, exiting the light exit, onto the sample);
   a second mirror which in a first position is aligned for reflecting the measuring light, reflected from the first mirror, to the receiver, and which in a second position is aligned for reflecting the measuring light, reflected from the sample, to the receiver.

6. The measuring system according to claim 5, wherein an axis of the receiver and the axis of the measuring light source are situated in parallel and are offset relative to one another.

7. The measuring system according to claim 5, wherein the first mirror is inclined at an angle of 45° with respect to the axis of the measuring light source.

8. The measuring system according to claim 5, wherein the second mirror in its first position is inclined toward the first mirror at an angle of 45° with respect to the axis of the receiver, and the second mirror in its second position is inclined toward the sample at an angle of 45° with respect to the axis of the receiver.

9. The measuring system according to claim 5, wherein the second mirror is pivotable between its first position, its second position, and a third position, the measuring system also including a fourth mirror that is situated on the side of the sample opposite from the first mirror, and is designed for reflecting the measuring light, reflected from the first mirror and transmitted by the sample, back to the sample and to the second mirror.

10. A measuring system for detecting an absolute reflection spectrum of a sample and for carrying out a reference measurement, comprising:
the measuring light source according to claim 1;
an optical receiver situated opposite from the measuring light source, for receiving measuring light;
a first mirror that is situated on an axis of the optical receiver and aligned for reflecting the measuring light, reflected from the sample, to the optical receiver; and
a second mirror which in a first position is aligned for reflecting the measuring light, exiting the light exit, to the first mirror, and which in a second position is aligned for reflecting the measuring light, exiting the light exit, to the sample.

11. The measuring system according to claim 10, wherein the measuring light source, the optical receiver, the first mirror, and the second mirror are designed to be situated together on one side of the sample.

12. The measuring system according to claim 10, wherein the second mirror is adjustable by pivoting the second mirror from its first position into its second position, and vice versa, an axis of pivoting the second mirror being situated perpendicular to the axis of the measuring light source and parallel to the surface of the sample, and the axis of pivoting the second mirror being situated between the axis of the measuring light source and the axis of the optical receiver.

13. The measuring system according to claim 10, wherein the second mirror is adjustable between its first position, its second position, and a third position, the measuring system also including a third mirror that is situated on the axis of the measuring light source and oriented toward the sample for reflecting the measuring light exiting the light exit, and the measuring system also including a fourth mirror that is situated on the side of the sample opposite from the third mirror, and is aligned for reflecting the measuring light, reflected from the third mirror and transmitted by the sample, back to the sample and to the first mirror.

14. The measuring system according to claim 10, wherein the second mirror is adjustable between its first position, its second position, and a fourth position, the second mirror in its fourth position being aligned in such a way that it reflects the measuring light, exiting the light exit, back to the light exit.

* * * * *